(12) United States Patent
Tamaro

(10) Patent No.: US 6,261,264 B1
(45) Date of Patent: Jul. 17, 2001

(54) SAFETY CAP ASSEMBLY FOR NEEDLES

(76) Inventor: Frank A. Tamaro, 22 Pancake Hollow Dr., Wayne, NJ (US) 07470

( * ) Notice: Subject to any disclaimer, the term of this patent is extended or adjusted under 35 U.S.C. 154(b) by 0 days.

(21) Appl. No.: 09/359,522

(22) Filed: Jul. 23, 1999

(51) Int. Cl.[7] .................................................. A61M 5/32
(52) U.S. Cl. ........................................... 604/198; 128/919
(58) Field of Search .......................... 604/110, 187–188, 604/192, 198, 263, 162, 158, 197, 199; 128/919

(56) References Cited

U.S. PATENT DOCUMENTS

| | | | |
|---|---|---|---|
| 991,015 | * | 5/1911 | Payne . |
| 2,559,474 | * | 7/1951 | Son . |
| 4,139,009 | * | 2/1979 | Alvarez . |
| 4,781,697 | * | 11/1988 | Slaughter . |
| 4,790,828 | * | 12/1988 | Dombrowski et al. . |
| 4,795,432 | * | 1/1989 | Karczmer . |
| 4,955,866 | * | 9/1990 | Corey . |
| 5,015,240 | * | 5/1991 | Soproni et al. . |
| 5,051,109 | * | 9/1991 | Simon . |
| 5,059,184 | * | 10/1991 | Dyke . |
| 5,411,492 | * | 5/1995 | Sturman et al. . |
| 5,423,766 | * | 6/1995 | Di Cesare . |
| 5,554,131 | * | 9/1996 | Lacivita . |
| 5,630,803 | | 5/1997 | Tamaro . |
| 5,779,684 | | 7/1998 | Tamaro . |
| 5,792,121 | | 8/1998 | Tamaro . |
| 5,807,352 | | 9/1998 | Tamaro . |
| 5,810,784 | | 9/1998 | Tamaro . |
| 5,817,070 | | 10/1998 | Tamaro . |
| 5,919,168 | * | 7/1999 | Wheeler . |
| 6,001,080 | * | 12/1999 | Kuracina et al. . |

FOREIGN PATENT DOCUMENTS

3808688 * 1/1989 (DE) .

* cited by examiner

Primary Examiner—Richard K. Seidel
Assistant Examiner—LoAn H. Thanh
(74) Attorney, Agent, or Firm—Carella Byrne Bain Gilfillan; William Squire

(57) ABSTRACT

A safety needle cap assembly for needles automatically caps the used needle the instant the needle is withdrawn from a patient. An elastic compressible sheath is attached to a safety needle cup shaped cap and is under compression with the cap in a retracted position exposing the needle tip for use. The cap is restrained in a rearward needle exposed state by one or more extension members extending rearwardly from the cap over the syringe hub. The extension may be a thin film, a string, a flexible rod or an articulated rod which are pressed against the hub by an outer packaging enclosure to retain the cap in the needle exposed state during shipping and handling prior to use. During removal of the enclosure for use of the needle, the extension is then pressed against the hub by the user in one embodiment, or a syringe grip or catheter body in other embodiments, holding the needle exposed ready for use. During use, the extension member is released while the needle is in the patient tissue and the needle remains exposed with the cap retracted. When the needle is removed from the patient, the elastic compression load on the cap is released, causing the safety needle cap to extend to its normal position and snap over the used needle tip automatically without operator assistance, the cap having a needle hole which displaces to an offset position when released to capture the needle in the cap cavity.

26 Claims, 12 Drawing Sheets

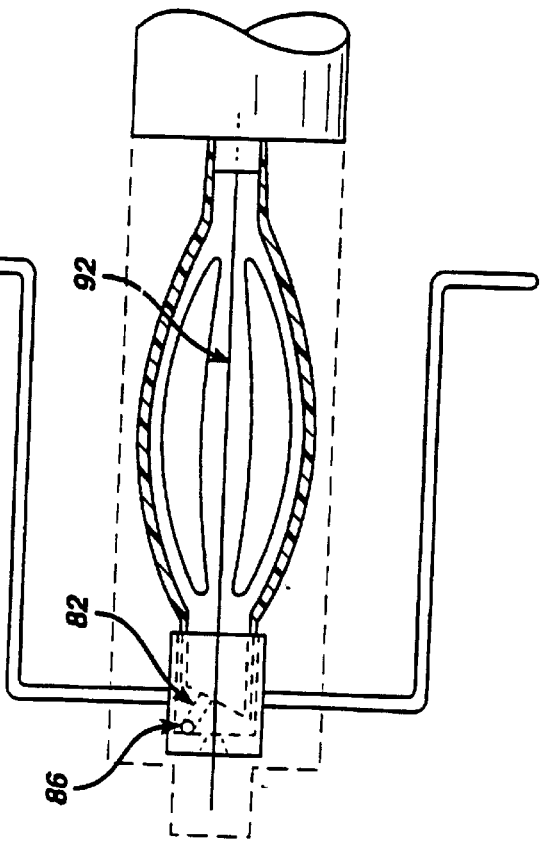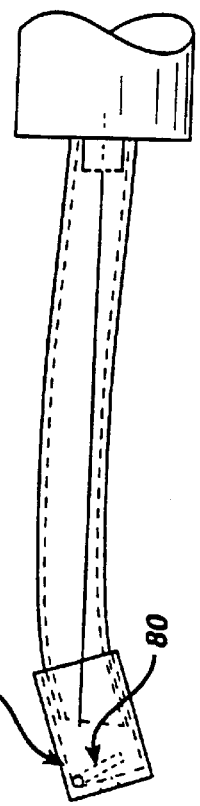

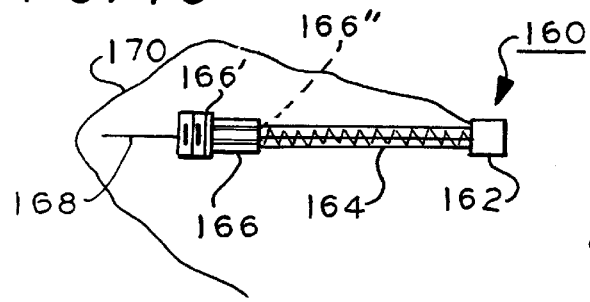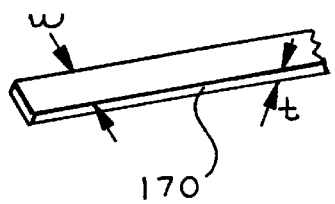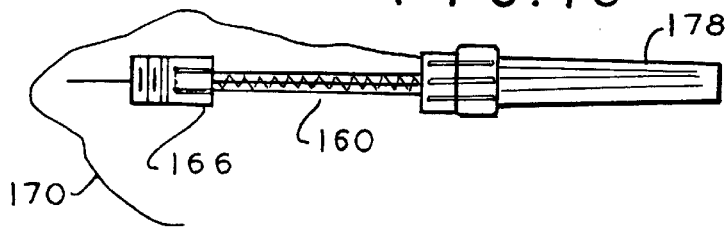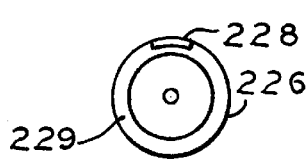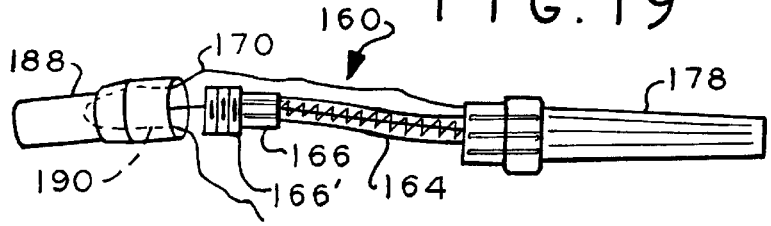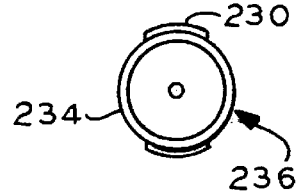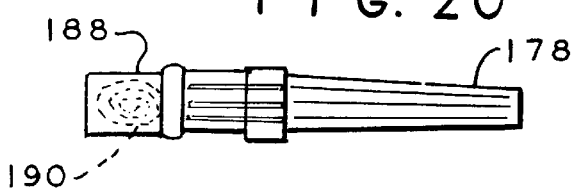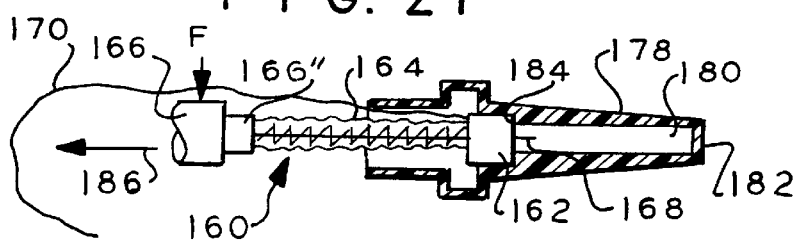

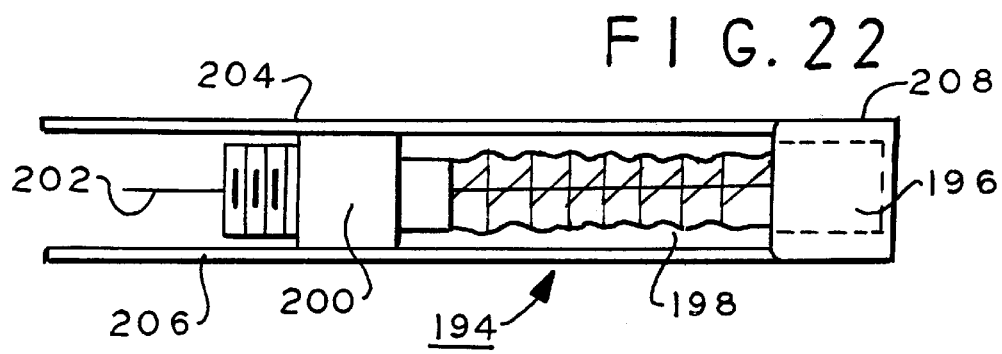
FIG. 22
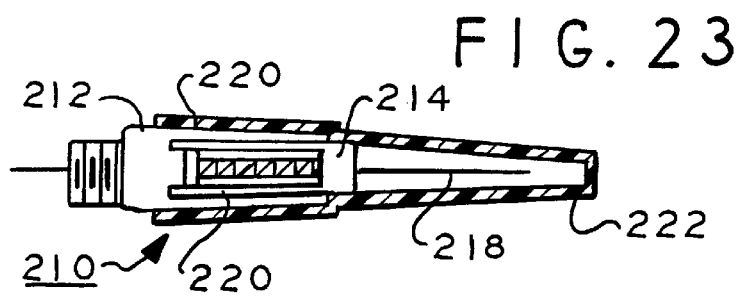
FIG. 23
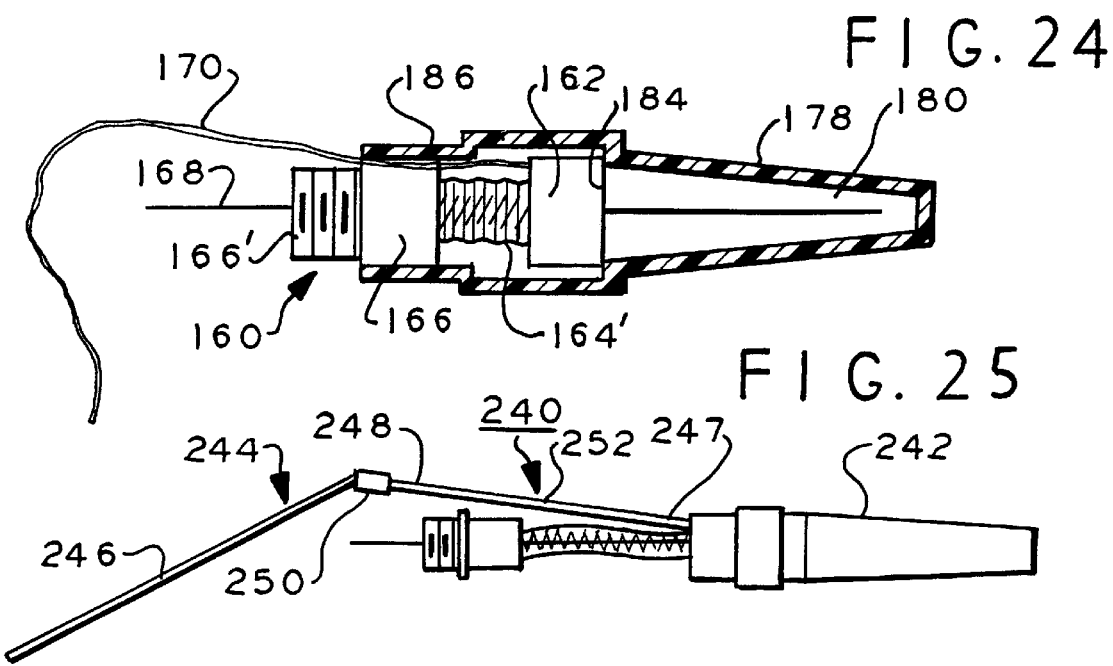
FIG. 24
FIG. 25
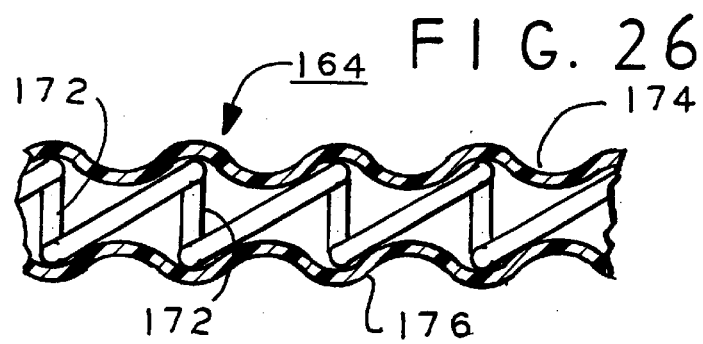
FIG. 26

SAFETY CAP ASSEMBLY FOR NEEDLES

CROSS REFERENCE TO RELATED PATENTS AND APPLICATIONS

Of interest are commonly owned U.S. Pats. Nos. 5,817,070, 5,630,803, 5,807,352, 5,810,784, 5,779,684 and 5,792,121 and commonly owned copending patent application entitled Safety Cap Assembly for Needles and Catheters Ser. No. 09/190,704 filed Nov. 12, 1998 in the name of Frank A. Tamaro, all of which are incorporated by reference in their entirety herein.

This invention relates to safety cap assemblies for needles, and in particular, safety cap assemblies for needles used in health-care related procedures.

Needles are employed in a wide variety of dental and medical procedures, including giving vaccines to patients, the injection of antibiotics, anesthetics, medicines, etc., the drawing of blood samples, intravenous feedings, and so on. Virtually all of these procedures subject medical personnel to the dangers of accidental sticking of the needle into a portion of their own bodies. The danger to the medical professional is primarily due to the possibility of accidentally injecting him or herself with an infectious pathogen derived from the patient after an injection has been delivered to the patient. At the present time, one need only mention the dread acronym "AIDS", (Acquired Immune Deficiency Syndrome) to understand the very real fears of the health professional.

Numerous devices have been suggested and employed to alleviate this problem. However, these devices and techniques require the knowledgeable, conscious cooperation of the physician, dentist or nurse. Any distraction at the moment a used needle should be safety capped can result in a needle remaining uncapped, and hence a danger to anyone who might come in contact with it. This invention overcomes these disadvantages by providing a safety cap for needles that automatically safety caps the needle at the precise moment the needle is withdrawn from the patient.

The present invention is an improvement of the invention disclosed in applicant's recently issued patent, U.S. Pat. No. 5,817,070

An object of the present invention is to provide a safety cap assembly for needles which automatically safety caps a needle at the moment the needle is withdrawn from a patient, thereby significantly reducing the possibility of accidental needle sticking the provider of the service.

A further object of the invention is to provide for automatic safety capping of used needles without the requirement of any operator attention.

An additional object of the invention is to provide for automatic safety capping of used needles without the requirement of any operator manipulation to accomplish this safety capping.

Still another object is to provide an automatic safety cap assembly for needles which is light in weight and inexpensive to manufacture.

An additional object of the invention, is to provide an automatic safety cap assembly that does not inadvertently expose a used needle.

Another object of the invention is to provide an automatic safety cap assembly for virtually any length and gauge of needle.

SUMMARY OF THE INVENTION

These and other objects are obtained in the instant invention of a safety needle cap for needles used in health-care related procedures.

A safety needle assembly according to an embodiment of the present invention comprises a hub; a hollow needle having a tip and defining a longitudinal axis, the needle being attached to the hub distal the tip; and a safety needle cap sub-assembly attached to the hub. The safety needle cap sub-assembly comprises a cap with a front wall and a depending sidewall defining a cup-shaped interior volume, the front wall having an opening therethrough for receiving the needle therethrough; a resilient compressible sheath attaching the cap to the hub along the needle axis, the cap having a first normal quiescent needle safety position wherein the cap opening is positioned beyond the tip relative to the hub and wherein the sheath is pliable such that the cap normally is positioned so that the opening is displaced offset from the needle longitudinal axis for capturing the needle tip in the cap interior volume, the cap having a needle ready second retracted position compressing the sheath so the sheath urges the cap toward the first normal needle safety position such that the needle passes through the cap opening and is exposed for use such that release of the cap from the retracted position permits the cap to displace to the first position; and an extension member extending solely rearwardly from and at the cap for restraining the cap in the needle ready second position.

In one aspect, an enclosure is included for the assembly including an outer wall defining a cavity for receiving the cap, sheath, hub and a portion of the extension member, a second portion of the extension member extending beyond the enclosure.

In a further aspect, the extension member is juxtaposed with the hub and is pressed to the hub by the enclosure to restrain the cap in the second position.

The extension member is preferably flexible and in a further aspect the extension member comprises a thermoplastic film.

In a further aspect, the extension is an elongated rod with at least one articulated joint. The extension member may be a relatively stiff elongated element.

In a further aspect, at least one further extension member is secured to the cap.

The extension member is preferably molded one piece integral with the cap. A safety needle cap assembly for use with a hub portion for holding a needle according to a further aspect, the assembly comprises a safety needle cap having at least a front face portion, and side wall means connected to the front face portion and extending in a rearward direction from the front face portion a minimum distance to a rear end.

In a further aspect, the elastic compressible sheath means receives the needle therethrough and has a first end connected to the safety needle cap and a second end for connection to the hub portion. At least one cap extension member is secured to and extends substantially in the rearward direction from the safety needle cap towards the hub portion. The front face portion of the safety needle cap has at least a first opening for receiving the needle therethrough. The safety needle cap is constructed to prevent the passage therethrough of the needle other than through the first opening, so that when the needle is attached to the hub portion, and when the needle is positioned within the elastic sheath means with the second end of the sheath means being connected to the hub portion in a pre-ready condition, and when the cap is positioned so that a first axis of the first opening in the front face portion of the cap is in axial alignment with the longitudinal axis of the needle, the needle within the cap can be passed through the opening in the front face portion of the cap to a ready position, the cap sliding in the rearward direction relative to the needle causing the elastic sheath means to be compressed so that when the needle is withdrawn during a procedure involving injecting the needle into a patient, and the compressed elastic sheath means is released, the cap is automatically urged forward by the releasing elastic sheath means over the tip of needle and beyond to a released condition, with the opening in the cap out of alignment with the axial alignment of the needle, the minimum distance that the side wall means extends in the rearward direction and the length of the elastic sheath means in the released condition being sufficient such that the tip of the needle in the pre-ready or released condition of the elastic sheath means is captured within a volume defined by the front face portion and the rear end of said side wall.

In a further aspect, the extension member is coplanar with the sidewall means. Preferably the extension member is a pliable film. The extension member and cap are preferably one piece integral thermoplastic material In a further aspect, the extension member extends rearwardly a distance sufficient to be juxtaposed with the hub.

In a further aspect, a hub is secured to the elastic sheath means rearwardly of and distal the cap, the extension member extending juxtaposed with and beyond the hub.

Preferably the extension member is secured radially outwardly of and to the sidewall means.

In a still further aspect, the extension member is an elongated pliable flap having a transverse width greater than its thickness.

In a further aspect, the safety needle cap further comprises a rear face portion disposed along the side wall means a minimum distance rearwardly from the front face portion and connected to the side wall. The rear face portion includes a second opening having a second axis, the second axis axially offset from the first axis. The second opening is adapted to cooperate with the needle so as to position the safety needle cap in the pre-ready and released conditions, in an orientation, such that the first opening is not axially aligned with the axis of the needle.

In a further aspect, the first opening is a frusto-conical-shaped opening, the opening on the inside surface of the front face portion being smaller than the opening on the outside surface of the front face portion.

Preferably the opening on the outside surface of the front face portion is of sufficient diameter such that body fluids adhering to the needle after withdrawal from the patient do not bridge the distance between the needle and the outside surface of the front face portion beyond the perimeter of the opening disposed on the outside surface of the front face portion.

In a still further aspect, an absorbent material is disposed in the frusto-conical opening.

In a further aspect, a hub is included with a needle attached to the hub and an enclosure is releasably secured to the hub about the needle, cap and a portion of the at least one extension member, the enclosure assembly disposed to enclose the safety needle cap and the elastic sheath means in the ready condition, the at least one extension member extending beyond the enclosure adjacent to the hub in a region between the hub and enclosure.

In a further aspect, the extension member is held to the hub by friction squeezing action of the enclosure to the hub.

Preferably the elastic sheath means comprises an elastomeric material.

In a further aspect, the sheath means comprises a spring enclosed in a sleeve of compliant material.

In a further aspect, the elastomeric material is formed in an arc in its quiescent state.

BRIEF DESCRIPTION OF THE DRAWINGS

FIGS. 10, 11(*a*), 11(*b*), 12(*a*), 12(*b*) depict in elevational views a modification to the safety cap feature of the invention.

FIG. 16 is a perspective view of a needle safety assembly according to a further embodiment of the present invention.

FIGS. 16*a*–16*b* are end views of different embodiments of safety needle caps and extension member attached thereto.

FIGS. 16*c* and 16*d* are isometric views of extension members according to further embodiments of the present invention.

FIG. 17 is a perspective fragmented view of an arm flap member of the embodiment of FIG. 16.

FIG. 18 is a perspective view of the assembly of FIG. 16 showing attachment of the front assembly casing enclosure secured to the safety cap portion of the assembly of FIG. 16.

FIG. 19 is a perspective side elevation view of the assembly of FIG. 18 showing an attachment stage of the rear assembly casing enclosure to the assembly of FIG. 18 with the arm flap member received partially in the rear casing enclosure.

FIG. 20 is a side elevation view of the needle assembly of FIG. 19 with the front and rear casing enclosures secured in the closed state with the needle assembly encased therein.

FIG. 21 is a fragmented sectional side elevation view of the safety cap portion of the assembly of FIG. 19.

FIG. 22 is side elevation view of a further embodiment of a safety cap needle assembly of the present invention.

FIG. 23 is side elevation partially in section view of a further embodiment of a safety cap needle assembly of the present invention.

FIG. 24 is a side elevation sectional view of the embodiment of FIG. 20 in an intermediate stage with the rear casing enclosure not yet attached.

FIG. 25 is a side elevation view of a further embodiment of a needle safety cap assembly according to the present invention.

FIG. 26 is a sectional side elevation view of a sheath according to an embodiment of the present invention.

DETAILED DESCRIPTION OF THE PREFERRED EMBODIMENTS

As noted above, the present invention has broad application. For purposes of illustration only the needle system to be described hereinafter will focus on the syringe system which includes a syringe barrel and plunger. The needle hub in this system can be formed as part of the barrel (not shown) or be separate therefrom and which, together with the needle, inserted typically into an opening in the syringe barrel. In addition, the needle system may be employed with catheters as well as for use with syringes used for injection of fluids into a body.

Figure 1:
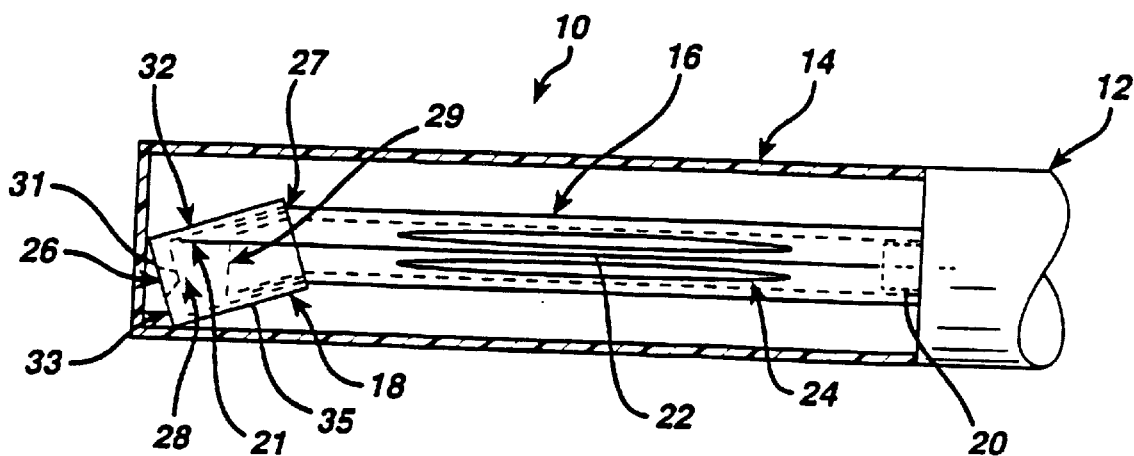
FIG. 1 is an elevational, sectional view of an embodiment of the safety needle cap assembly of the present invention.

Turning now to the drawings wherein similar structures, having identical functions, are denoted with the same numerals, FIG. 1 illustrates a safety needle cap assembly 10 of the present invention. A syringe 12 is shown with an attached needle 22. The needle 22 is shown enclosed within an elastic sheath 16, the elastic sheath being connected at one end to the hub 20 of the needle, and at its other end to a safety needle cap 18. The sheath 16 comprises a plurality of elongated elastic, elastomeric or plastic material, strips, for example, four, joined at each end. The strips can be collapsed longitudinally along the needle 22 longitudinal axis and when released, return to their normal extended state.

The sheath 16 may be molded and is attached to the safety cap by any convenient means, such as with suitable adhesives, clips (not shown), etc. Where the elastic sheath is formed of an elastomeric material such as latex, the connection can be made by any suitable mans including a frictional fit between the two pieces. The elastic sheath 16 can be fabricated in a variety of suitable elastomers, e.g. latex rubbers, capable of being easily compressed under tension, and including a good "memory" so as to enable the elastic sheath 16 to return to its original shape when the tension is released. Other resilient elements, for example, a spring, can be employed as the elastic sheath as will be more fully described and illustrated in FIGS. 6, 6A and 7.

The safety needle cap 18 itself can be fabricated out of a number of hard materials, which will be impenetrable to the needle tip, for example, a clear plastic such as polycarbonate. The shape and size of the safety needle cap can vary depending on applications and design preferences, a tubular shape being suitable for some applications as depicted in FIG. 1 See also FIG. 15 and the attending description.

The tubular shaped safety needle cap is shown fully open at one end 27 for attachment to the elastic sheath 16. As is the case with the needle hub 20, the other end of the elastic sheath 29 can be attached to the safety needle cap by any convenient means, such as with a suitable adhesive, clips (not shown), frictional fit, etc. The other end of the safety needle cap is closed except for an interior opening 28 within the cap of just sufficient diameter as to permit the passage of the syringe needle 22 through this opening. Of course, if the cap is made of compressible material the opening 28 may also closely receive the needle which may expand the opening as the needle passes therethrough. As will be more fully illustrated and explained, the cap is an important feature of the invention. It virtually precludes the possibility of inadvertent, reemergence of the tip 21 of the needle after the needle 22 has been used.

The exterior portion 26 of the interior cap opening 28 is an enlarged frusto-conical shape. It precludes body fluids on the needle from contacting the surface 31 of face portion 33. Gauze or other absorbent mesh material, (see FIG. 14(a) and FIG. 14(b)) can be secured within the frusto-conically shaped opening 28 to absorb any remaining body fluids on the exterior of the needle as the needle retracts to within the cap after use.

The safety needle cap 18 is affixed to the end of the elastic sheath 16. The length of the sheath between its points of attachment to the cap 18 and the hub 20 is such that the needle tip is enclosed in the volume defined by the face portion of the cap 33 and the annular sidewall 35 when the sheath 16 is in its released condition, i.e., not under compression forces. In this relaxed state, the needle opening 28 within the cap is offset from the axial alignment of the syringe 12 and attached syringe needle 22. This arrangement positions the tip 21 of the needle along the upper wall 32 of the tubular side wall of the cap 18. The elastic sheath 16 is shown as a tube of latex, silicone or other material having slits 24, if necessary, along a portion of the length of the elastic sheath so as to facilitate compressing the sheath when required. The slits can also facilitate a "drooping" of the cap end of the sheath out of alignment with the needle 22 when the system is in the released condition. Where elastomeric material is used, the requirement for slits will depend in part on the gauge, thickness, density etc. of the material. the entire safety needle cap 18, elastic sheath 16 and syringe needle 22 are shown enclosed in a sterile enclosure 14 which is removed at an appropriate time before use.

Figure 2:
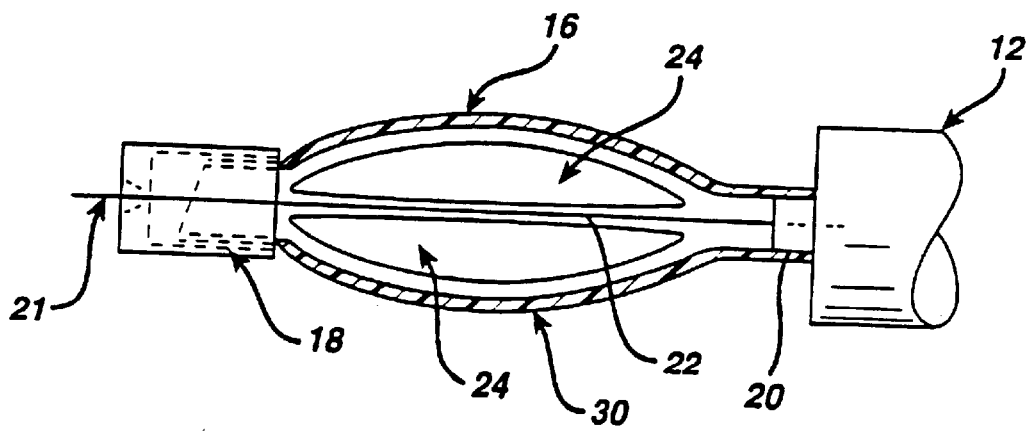
FIG. 2 is an elevational, partial sectional view of the embodiment of the safety needle cap assembly of FIG. 1 illustrating the device ready for use.

FIG. 2 illustrates the embodiment of the invention depicted in FIG. 1 now ready to be utilized with a patient. The sterile metal foil 14 outer casing has been removed, and the safety needle cap 18 has been manually moved (not shown) so that the needle opening 28 in the cap is in axial alignment with the hypodermic needle 22, the cap being moved longitudinally along the axis alignment with the needle, causing the elastic sheath 16 strips 30 to be compressed and therefore under compression load, while at the same time exposing the tip 21 of the needle 22. With the hypodermic needle 22 in this position, the needle can now be inserted into the patient to perform the required medical procedure.

Figure 3:
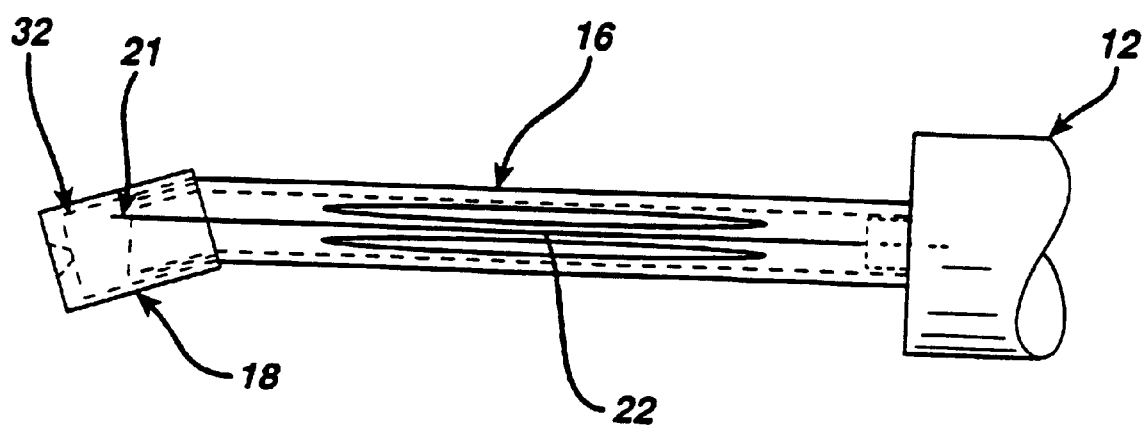
FIG. 3 is an elevational view of the device shown in FIGS. 1 and 2, illustrating the position of the safety needle cap after use.

FIG. 3 illustrates the embodiment of the invention depicted in FIGS. 1 and 2 after the needle has been withdrawn from the patient. This procedure is best understood from FIGS. 8 and 9. The moment the needle is withdrawn from the patient, the elastic tension within the elastic sheath 16 is released which causes the safety needle cap 18 to snap extend to its original position. During returning of the cap to its original position, the hypodermic needle 22 is caused to be located relative to the cap 18 in a position within the cap interior, with the tip 21 of the needle now harmlessly in contact with the inner surface of the upper wall 32 of the safety needle cap 18. The syringe 12 and needle 22 combination including the safety needle cap 18 and elastic sheath 16 can now be disposed of safely. It is to be noted that the securing of the now potentially dangerous hypodermic needle within the safety needle cap of the invention is accomplished without any manual manipulations by the health professional, or even active consciousness of performing this often extremely important safety procedure.

Figure 4:
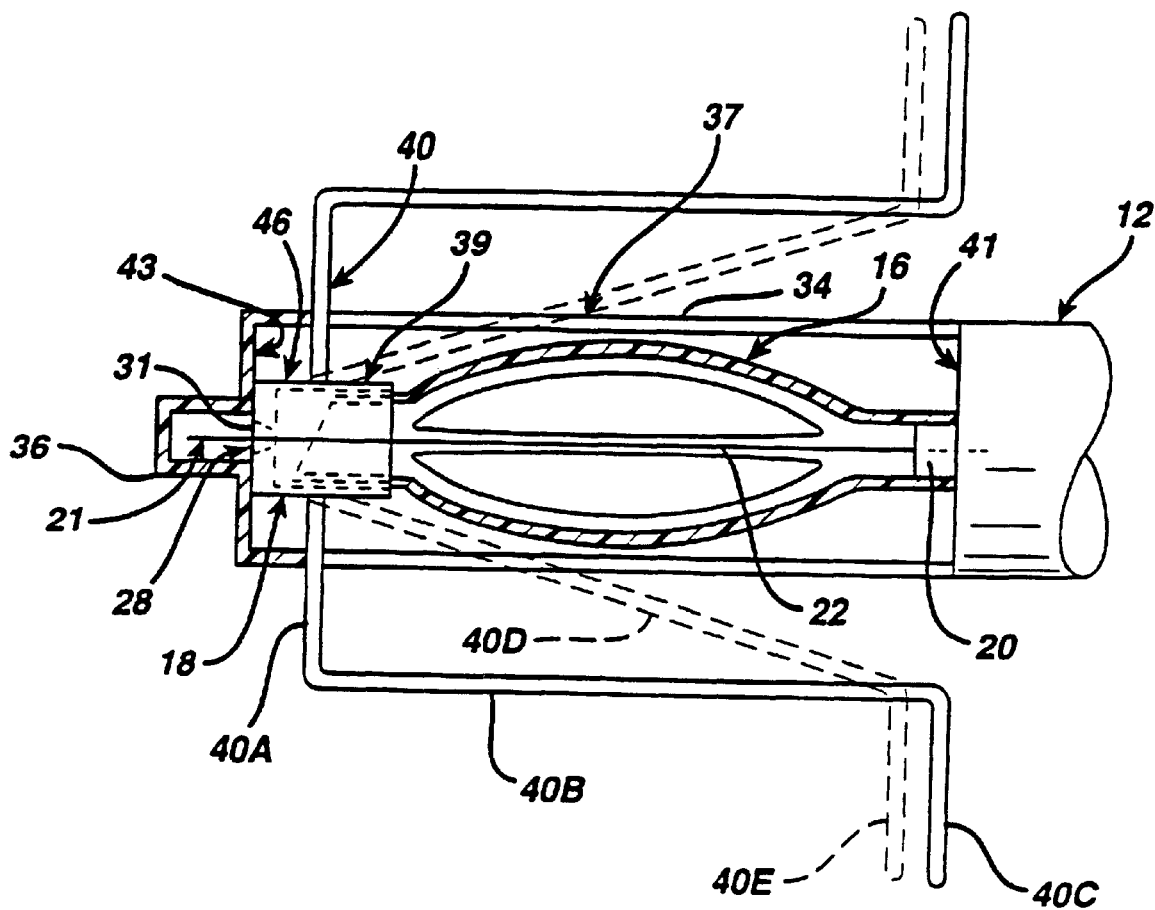
FIG. 4 is an elevational, partial sectional view of an embodiment of the invention, showing a safety needle cap assembly enclosure and modified safety needle cap position the needle in ready for use, axial alignment with the needle opening within the cap. Projecting arms extending outwardly from the safety needle cap and rearwardly towards the needle hub are depicted.
Figure 4A:
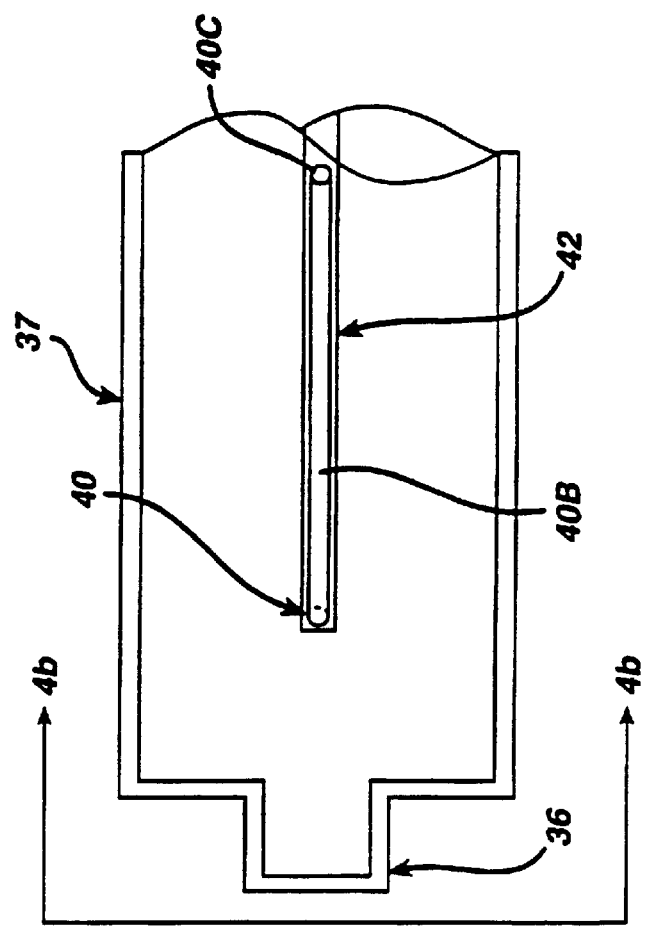
FIG. 4A is a top plan view of the safety needle cap assembly enclosure and syringe depicted in FIG. 4.
Figure 4B:
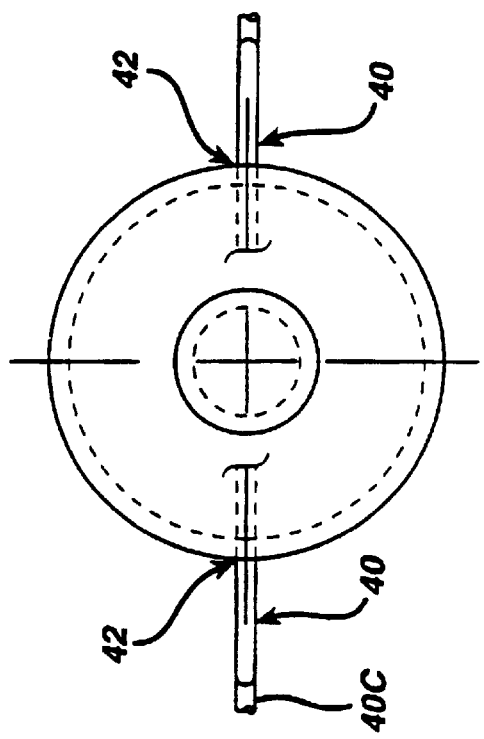
FIG. 4B is a view of the cap assembly of FIG. 4A taken along lines 4B—4B in that view.

FIG. 4 illustrates a second embodiment of the invention in which a safety needle enclosure assembly 37 cooperates with a modified safety needle cap 39. The modified safety needle cap 39 includes arms 40 attached to and projecting radially outward from the side wall 46 of the modified cap. The attached arms 40 project through slots 42 in the safety needle enclosure assembly 37 (FIG. 4A). The axial length of the enclosure assembly 37 and length of slots 42 are such that, when the assembly 37 and length of slots 42 are such that, when the assembly 37 and sheath-cap combination 16-39 is in place on the syringe-needle combination, with the one end of the sheath 16 secured to the needle hub 20, the arm 40 cooperate with the closed ends of the slots 42 to maintain the elastic sheath in a retracted condition under elastic compression. The safety needle enclosure assembly 37 can be fabricated in any of a variety of plastic materials. The safety needle enclosure assembly 37 can have a smaller diameter tubular extension 36 sealed at one end, forming a safety cover for the now exposed tip 21 of the needle. The smaller diameter tubular extension 36 is confluent with a larger diameter tubular extension 34. The open end of the latter contacts the syringe barrel at surface. 41 when the assembly-cap-sheath combination 37-39-16 are assembled.

The enclosure 37 including its length and the relative diameter of tubular extension 36, can be designed so that the outside surface of the face portion of cap 39 (corresponding to surface 31—see FIG. 1) contacts the interior surface of the vertical section (as seen in FIG. 4) disposed between the tubular extensions 34 and 36 and before arms 40 ever reach the closed ends of the slots. This design, alternately, can maintain the safety needle cap assembly in a ready condition.

The arms 40, in this modification, include a first portion 40A which extends in a radial outward direction from the safety needle cap 18. A second portion 40B extends rearwardly of the first portion 40A, towards the needle hub 20. A third portion 40C, the finger grip portion, similarly extends in a radial outward direction from the body of the assembly.

With this modification to the arm structure disclosed in the aforementioned patent, U.S. Pat. No. 5,630,803, incorporated by reference herein, the operator's fingers are positioned further back along the axis of the needle, in the direction of the needle hub, when the assembly is in the ready condition. This facilitates the use of the system and is particularly advantageous in the field of dentistry.

Shown in phantom in FIG. 4 is a further possible embodiment of the arm structure in keeping with the present invention. In this variation, the arm portion 40D extends inclined to the needle outwardly from the assembly and rearwardly in the direction of the hub 20. Finger grip portion 40E extends outwardly from its connection to portion 40D.

To use the device illustrated in FIGS. 4 and 4A once the sheath is connected to the hub 20, the operator grasps the arms 40 extending through the slots 42 in the safety needle enclosure assembly with his or her fingers at finger grip portions 40C or 40E. The operator then pulls the safety needle enclosure 37 off from its contact with the syringe barrel with his or her free hand. The operator holds the cap 18 rearwardly with the grip portions as the enclosure 37 is removed. With the tip 21 of the needle 22 now exposed through the cap 18, the operator can now proceed with the medical procedure.

Figure 5:
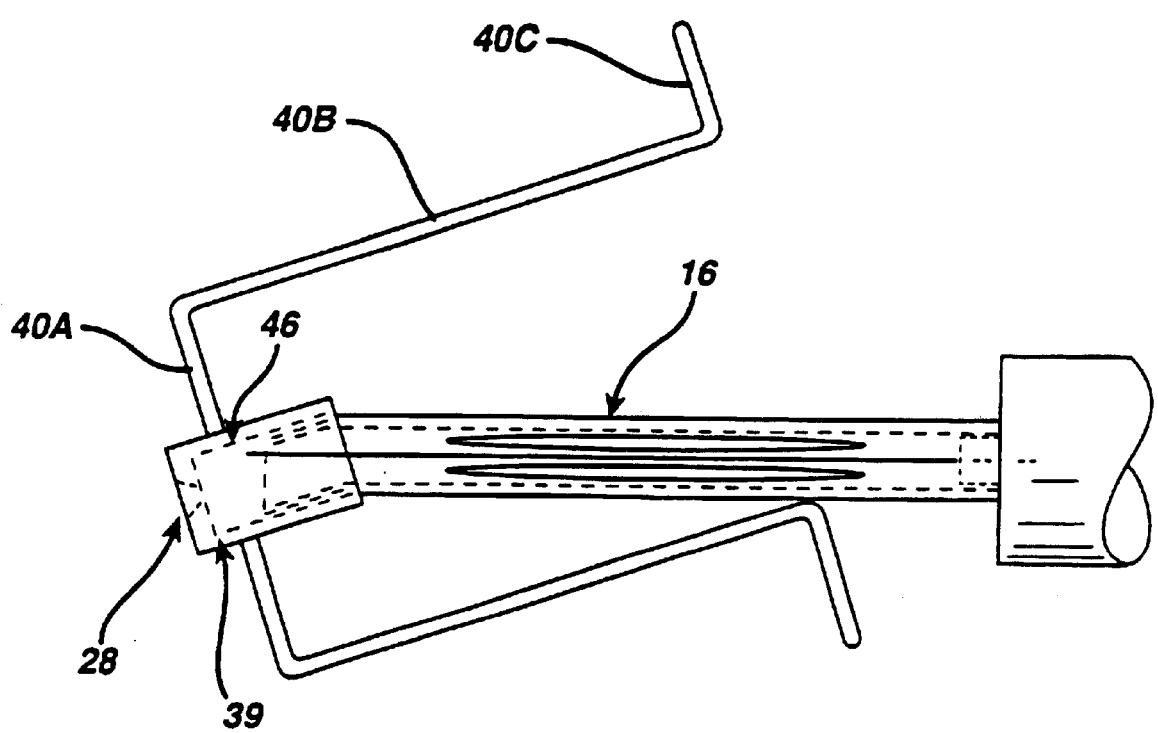
FIG. 5 is an elevational view of the invention depicted in FIG. 4 illustrating the position of the safety needle cap after use.

As shown in FIG. 5, after the needle is withdrawn from the patient, the elastic tension is released in the elastic sheath 16 which causes the modified safety needle cap 39 to move forward to a position where it encloses the needle tip, the tip of the needle now rests within the cap on the inside surface 46 of the side wall.

Figure 6A:
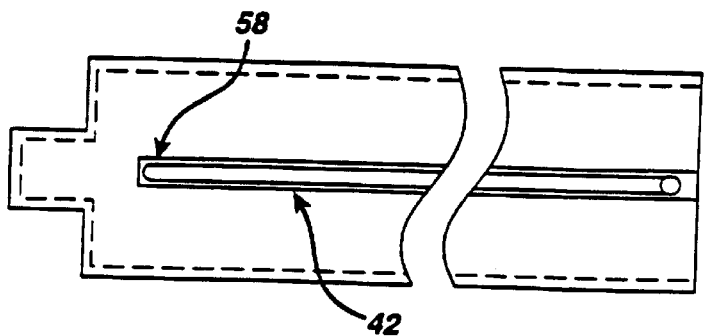
FIG. 6A is a top plan view of a part of the safety needle cap assembly enclosure and syringe depicted in FIG. 6.
Figure 6:
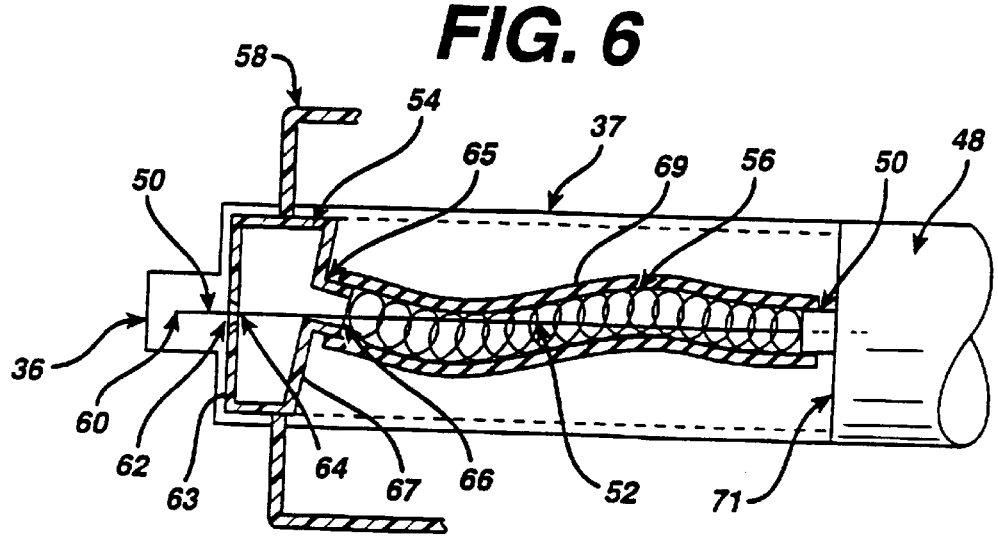
FIG. 6 is an elevational, partial sectional view of an embodiment of the invention which employs a spring for the elastic sheath means, and depicts a second embodiment of the safety needle cap means.
Figure 7:
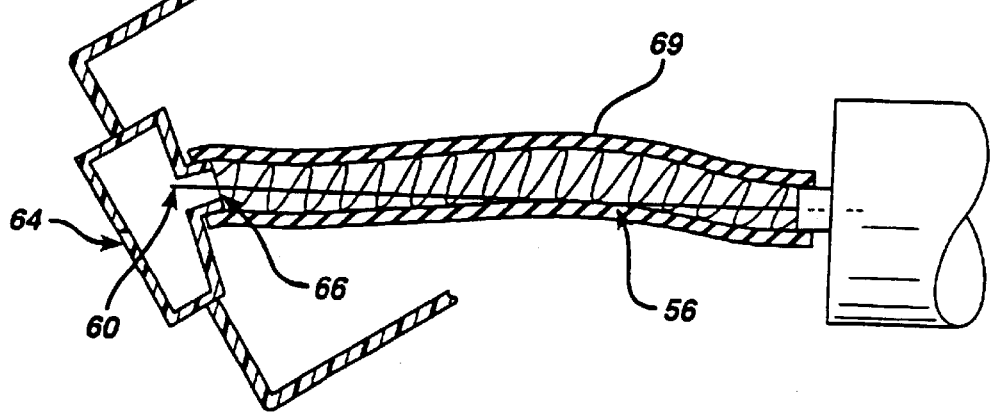
FIG. 7 is an elevational view of the invention depicted in FIG. 6 showing the position of the safety needle cap after use.

In FIGS. 6, 6A and 7, a further embodiment of the invention is illustrated depicting the use of a spring elastic sheath 56 and illustrating a further modified safety needle cap 54. The sheath 56 comprises a central inner preferably metal coil compression spring and an outer collapsible thermoplastic tubular film sleeve 69. The sleeve 69 may have annular extending undulations to assist in its collapsing in the axial direction.

As described above in respect of FIGS. 4 and 4A, a safety needle enclosure assembly 37 encloses the further modified cap 54 and spring elastic sheath 56. One or more arms 58 on the further modified cap project through matching slots 42 in the safety needle enclosure assembly, thereby putting compression load on the spring sheath 56. Needle 50 is aligned with rear opening 66 in the cap 54. The needle is axially aligned with a smaller internal needle opening 64 and a larger exterior frusto-conical needle opening 62 in a front face portion 63 of cap 54 so that the needle extends through the cap with the tip of the needle 60 now exposed beyond the cap 54, but protected by the tubular extension 36 of the safety needle enclosure assembly 37. The principal modification shown to the cap 54 is that, instead of having a fully opened rear portion of the cap as described in FIGS. 1–5, the rear portion of the cap is substantially closed, by a back face portion 67 which includes a tubular extension 65 having an opening 66. One end of the spring sheath 56 is attached to the tapered tube 65 in any convenient manner, such as adhesively or with a clamp (not shown) with the other end of the spring 56 similarly attached to needle hub 50. The inner coil spring can be enclosed optionally in sleeve 69 made of compliant material such as a fabric, nylon or the like, or even an elastomeric material, such as latex or thermoplastic material. One end of the sleeve 69 is attached to the extension 65 and the other end to needle hub 50. The inner coil spring of sheath 56 itself can be fabricated in a variety of suitable materials, including metal or plastic.

As can best be seen in FIG. 6 with the arms 58 secured in the slots 42 within the safety needle enclosure assembly 37 and the one end of the assembly 37 in contact with the surface 71 of the syringe 48, the spring sheath 56 is put under elastic compression. The needle 42 enters the cap through the opening 66 in the tubular extension 65 of the cap 54 and is axially aligned with the internal needle opening 64 and external needle cap opening 62, with the tip 60 of the needle now protruding into the smaller diameter end portion 36 of the safety needle enclosure assembly 37. Operator manipulations and grasping of the arms 58 and removal of the safety needle enclosure assembly 37 now permits direct utilization of the syringe 48 in the delivery of a medial procedure to a patient. In this mode the needle tip 60 remains exposed by the retention of the cap rearwardly relative to the needle in the presence of the compression load of the sheath 56 by the simultaneous manual grasping of the arms 58 and the syringe 48.

As illustrated in FIG. 7 after the needle is withdrawn from the patient, the spring compression load is released by releasing the arms 58, which release results in the stored energy propelling the cap forward beyond the needle tip. The tip 60 of the needle now automatically is positioned within the cavity of the further modified safety needle cap 54. The opening 62 in the front of the cap and the opening 66 at the rear of the cap are now misaligned with the needle axis to a degree that virtually precludes any possibility of accidentally realigning the needle with the openings 62.

Figure 8:
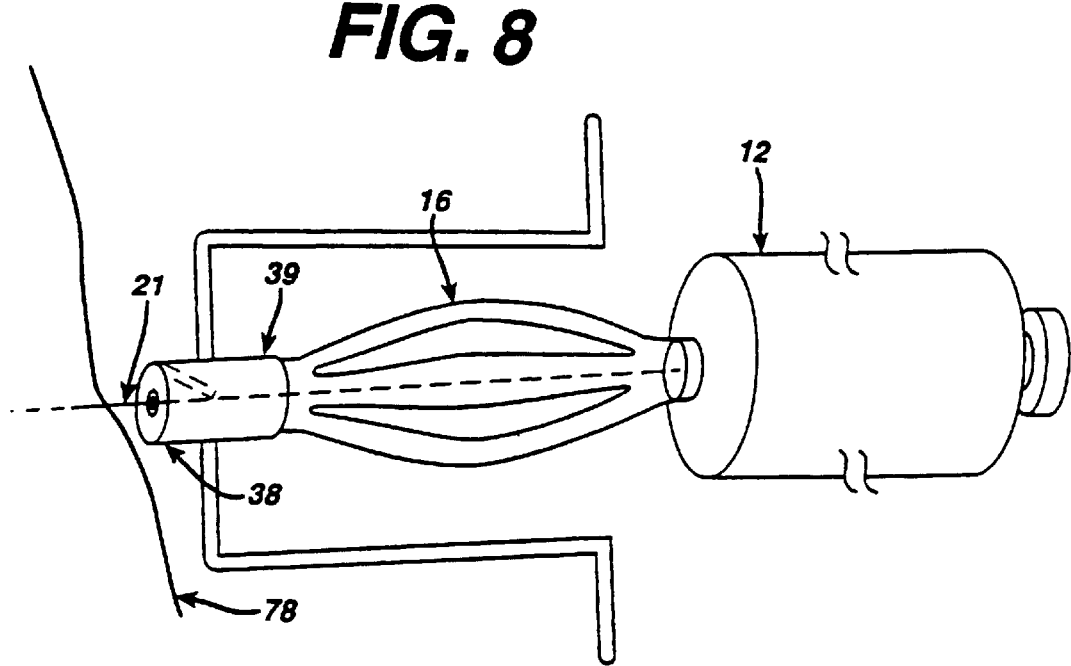
FIG. 8 is a perspective view of an embodiment of the invention as being used to deliver an injection to the arm of a patient.
Figure 9:
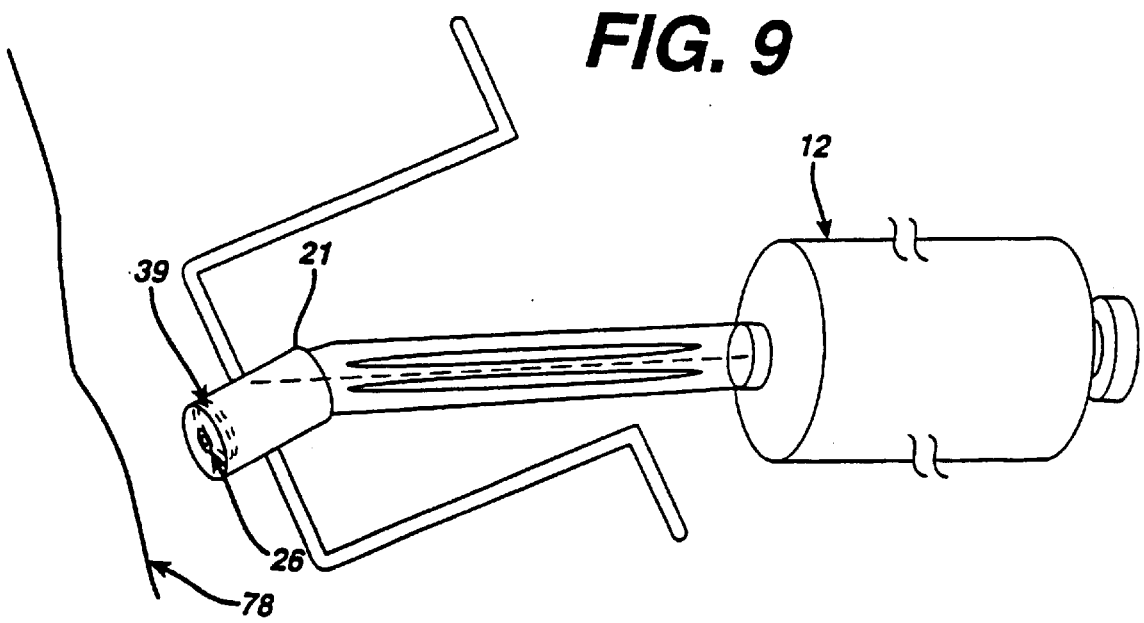
FIG. 9 illustrates the embodiment of the invention as depicted in FIG. 8 after the needle has been withdrawn from the patient's arm.

FIGS. 8 and 9 illustrate the second embodiment of the invention depicted in FIGS. 4, 4A and 5 in actual use on a patient. The tip 21 of the needle is shown penetrating the skin on the arm 78 of a patient with the lower bottom edge 38 of the tubular shaped modified safety needle cap 39 in contact with the skin. This serves to aid in maintaining the cap in a withdrawn position, thus sustaining the compression load in the elastic sheath 16 while a medical procedure is in progress. Once the procedure is completed and the needle withdrawn, FIG. 9, the safety needle cap automatically extends due to the energy in the compressed sheath 16 and snaps over the tip of the needle, safely enclosing the potentially dangerous needle.

Figure 10:
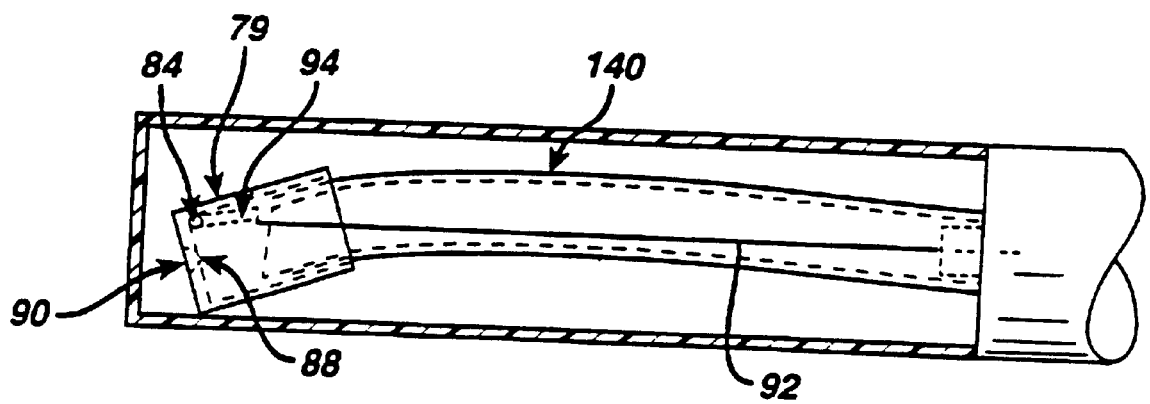

FIGS. 10 through 12 depict supplementary adaptations of the cap which, if necessary, could be used in the alternative to ensure the capture of the needle tip after use. FIGS. 10, 11(a), (b) and 12(a) (b) illustrate a modified embodiment of a safety cap 79. This modification depicts the incorporation of a closure 80 including a flap 82 hinged at hinge 84 to the sidewall 86. The flap 82 is of sufficient size and hinged to the sidewall in a manner that it closes off the interior side 88 of the opening 90 when the cap is in its extended safety position as shown in FIGS. 12(a) and 12(b). FIG. 10 shows the relationship of the flap 82 to the needle 92 when the cap-sheath assembly is first connected to the needle-syringe assembly. The needle contacts surface 94 of the flap and captures the flap 82 between itself and the sidewall 96. This permits the subsequent operation of aligning the needle 92 with the opening 90 in readying the syringe-sheath assembly for use.

FIGS. 11(a) and 11(b) indicate the relationship when the needle is axially aligned and positioned through the opening 90. In this view, the flap 82 rests on the surface of the needle 92.

The hinged flap can be included as part of the plastic mold used in forming the cap so that the formed cap product would include the flap as an integral one piece part. The flap can be employed with any of the caps 18, 39 and 64 described above or as described below in FIG. 15.

Figure 13:
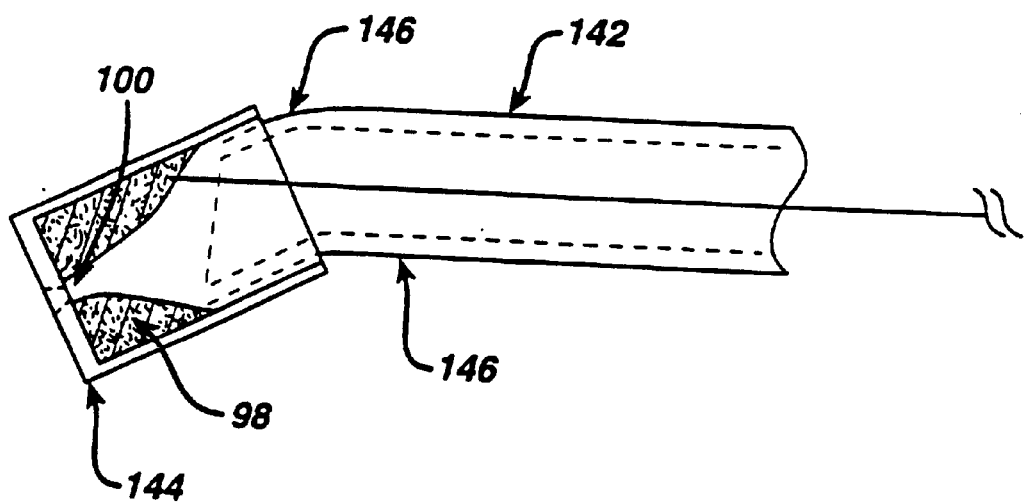
FIG. 13 depicts yet another modification of the safety cap feature of the invention; and, in adaptation of the elastic sheath means portion.

FIG. 13 illustrates the use of an annular ring 98 of Styrofoam or similar material to capture and retain the needle point after the medical procedure. The ring 98 is placed inside the cap 144 and secured with appropriate means such as adhesive, at the juncture between the sidewall and interior surface of the face portion of the cap 144. The annular ring 98 as positioned and constructed of course, would permit needle access to opening 100 during set up.

Figure 14A:
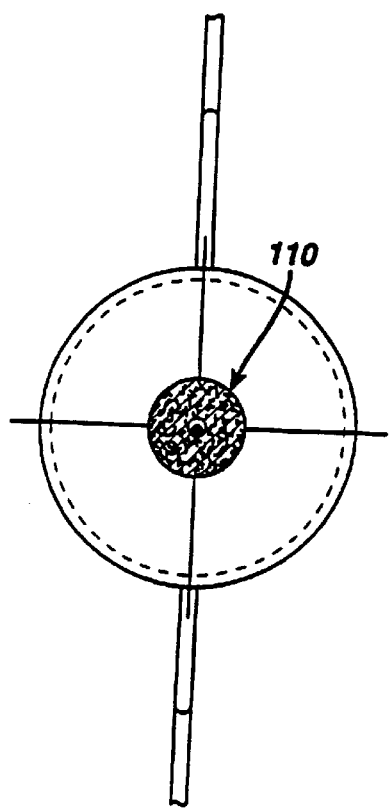
FIGS. 14(*a*) and 14(*b*) depict in front elevational and side, sectional elevational views the details of one embodiment of the safety cap feature of the invention.
Figure 14B:
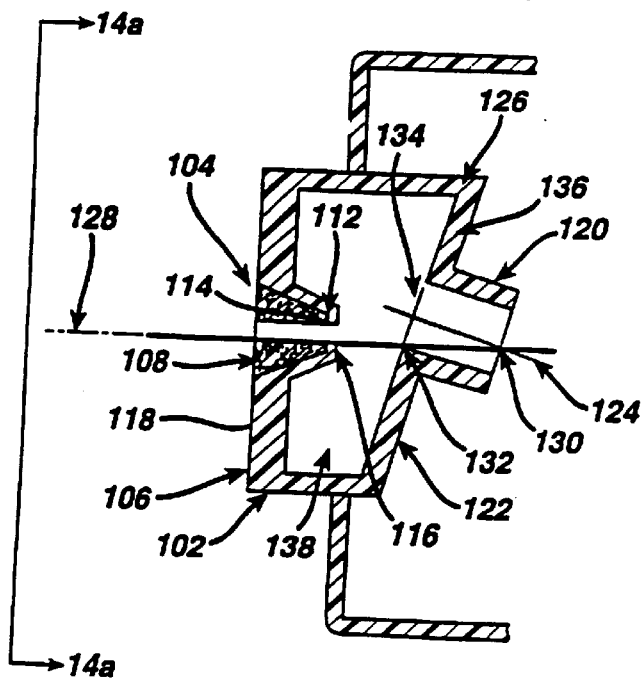

FIGS. 14(a) and 14(b) disclose in more detail a cap 102 which depicts the preferred construction of the frusto-conical opening 104 in the front face portion 106 and gauze 108 or other similarly, absorbent material disposed in the opening 104. The gauze is positioned in the frusto-conical opening and secured by a suitable adhesive. Although the cap style depicted is similar to cap 54 above, the configuration of the opening 104 is also appropriate for the front face portion of any cap configuration including caps 18 and 39 described earlier or as described below for the cap of FIG. 15.

The opening 104 includes a first, larger opening 110, which tapers rearwardly to a second opening 112, which may be further reduced in size to a third opening 114 by an annular radial inward extending flange 116. The flange 116 may be included in the cap design, if necessary, to facilitate the placement and retention of the gauze 108. The third opening 114 is of sufficient diameter to permit passage therethrough of the particular needle to be used. Preferably the diameter of the first opening 110 is sufficiently large, so that droplets of body fluid which may adhere to the needle as it is withdrawn from the patient do not bridge the space between the needle and the outer surface 118 of the face portion 106.

FIG. 14(b) is also helpful in illustrating an important feature of the style cap depicted (and style of cap 54 of FIG. 6). Tubular extension 120 formed in back face portion 122, is centered on axis 124 which is offset in relation to the axis of the frusto-conical opening 104 on the front face portion. Both before readying the cap-sheath assembly and the needle-syringe assembly prior to use, and after withdrawing the needle from the patient when the sheath relaxes and the needle tip is captured within the volume defined by the cap front face portion 106, rear face portion 122 and the sidewall 126, the tubular extension 120 serves a useful purpose. The tubular extension 120 and more particularly the angular orientation of rear face portion 122 in relation to the front face portion, ensures that the needle is oriented in a direction essentially parallel to axis 124, and necessarily is offset relative to the axis 128 that the needle aligns itself to when it is inserted through the opening 114.

In effect, the cap 102 pivots about the needle 130 at point 132 of the opening 134 on the interior surface 136 of the rear face portion 122 whenever the needle tip is positioned in the interior volume 138 as defined by the face portions and sidewall. This occurs, again, prior to readying the assembled capsheath-needle-syringe assembly and after the relaxed sheath moves the cap forward, after use, and the needle enters the volume 138, offset from axis 128. This precludes reentry through opening 114.

In FIGS. 10 and 12(b), assume the sheath 140 is fabricated from an elastomeric material such as latex. For the particular cap illustrated and that of caps 18 and 39 discussed above, i.e., caps without the rear face portion such as 122 in FIG. 14(b), it is of benefit, depending on its thickness and material, that the elastomeric sleeve of the sheath tends to arc, as depicted, due to the weight of the cap when the needle withdraws into the interior volume of the cap. Thus, in this relaxed state the effect of gravity can cause the cap end of the sheath to droop or arc so that the needle opening 100 within the cap is offset from axial alignment with the needle 92. Alternately, the elastomeric sleeve can be initially formed at the point of manufacture to include the arc. This inherently results in the opening in the cap, 90 being offset to the axis of the needle, thus advancing the purposes f the invention.

FIG. 13 depicts an alternate sheath 142. The sheath 142 in this embodiment is fabricated with a suitable bend 146 formed in the material to ensure that opening 100 will be offset from the needle axis when the needle tip is positioned within the cap volume.

Figure 15:
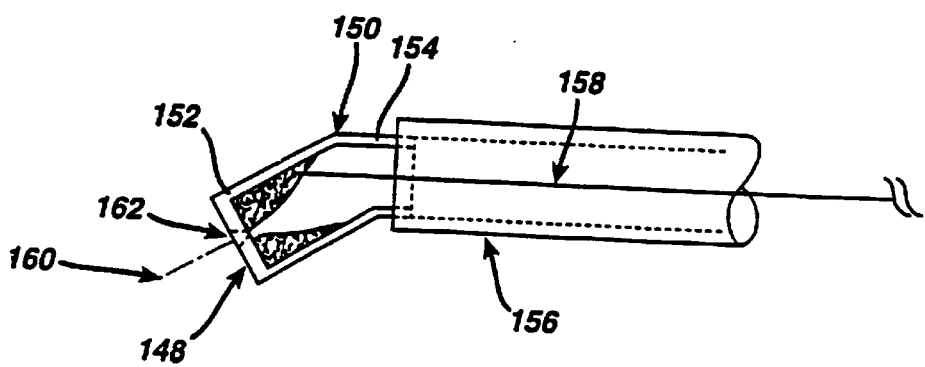
FIG. 15 is a partial, elevational view depicting a further embodiment of the safety cap which is formed in an elbow configuration to accommodate the purposes of the invention.

In order to provide the offset from the needle axis as required, yet another embodiment as seen in FIG. 15 depicts the cap 148 as fabricated with an angular offset 150 between a front portion 152 and rear portion 154. Here, of necessity, irrespective of the orientation assumed by the sheath means 156 in the relaxed condition, the needle 158 is offset from the axis 160 of the opening 162. The needle is thus precluded from re-entering the opening inadvertently.

In FIG. 16, a further embodiment includes needle safety cap assembly 160 comprising a safety needle cap 162, a sheath 164, a hub 166 and a hollow needle 168. The hub 166 has a threaded end portion 166' (opposite the reduced diameter portion 166" receiving the sheath 164) for attaching the hub to a syringe barrel (not shown) or other device to which the needle is to be attached. A pliable elongated flexible extension member 170 is attached to the cap 162 and extends from the cap at the cap only in a rearward direction toward the hub 166. The cap 162 can have the shape and configuration of any of the embodiments described hereinabove in connection with FIGS. 1, 6 and 10 and alternatives as discussed above. The sheath 164 preferably has the configuration of the embodiment of the sheath 56, FIG. 6 or as described below in connection with FIG. 26.

In FIG. 26, sheath 164 comprises an inner preferably metal compression coil spring 172 and an outer sheath member 174. The outer sheath member 174 is tubular thermoplastic, for example, polyethylene or elastomeric material that is relatively thin, e.g., 0.005–0.025 inch thick film material. Such material is commercially available. Preferably the sheath member 174 is corrugated with annular undulations 176. The coil spring 172 abuts and is fastened to the cap 162 in the cap interior or at the cap side wall according to a given implementation or may be one piece molded. This is shown by way of example in the embodiment of FIG. 6 where the spring abuts the cap of this embodiment at an interior extension 66 at one end and abuts and receives the reduced diameter hub portion 50 at the other end. The sheath outer member 174 may be shrunk fit over the spring 172 somewhat forming undulations 176. The spring may be force fit into the member 174 in the alternative. The undulations permit the member 174 to readily collapse accordion style in the axial direction of the needle 168 longitudinal axis.

The extension member 170, FIG. 24, may take several forms preferably as a strip thin film sheet material such as employed in conventional rolled adhesive tape made of celluloid, cellophane or other thermoplastic film materials. This material is pliable and flexible and is easily folded, bent or rolled as needed. The member 170, FIG. 17, has a width w greater than its thickness t which may be about 0.001–0.020 inches, for example. The member 170 has a length greater than that of the assembly 160 as shown in FIG. 16. However, the length should be at least sufficient at its minimum value so that it is at least juxtaposed with the hub 166 for the reason explained below.

In FIG. 18, an intermediate stage of packaging the safety needle cap assembly 160 with an outer front outer enclosure 178 is illustrated. The enclosure 178 is an elongated hollow somewhat tubular structure having a cavity 180, FIG. 21. The enclosure is molded thermoplastic material, which may be transparent, and which may be of conventional design normally for packaging syringe needle and hub assemblies of standard conventional designs. In FIG. 21, the enclosure 178 cavity 180 is tapered with its narrow diameter at end 182. The enclosure has a shoulder 184 in the cavity 180. The cap 162 abuts the shoulder 184 and the needle 168 extends through the cap opening in the needle ready position. The sheath 164 is compressed at this stage and normally as compressed provides a compression load on the cap urging the cap 162 toward enclosure end 182.

Because there is an axially directed compressive force presented by the sheath 164, the hub 166 normally would tend to extend to the left in the drawing in direction 186. To prevent the sheath from extending in direction 186 and maintain the sheath compressed, the extension member is pressed against the hub juxtaposed therewith by a force F. This force may be provided by a person's fingers by squeezing the extension member 170 against the hub 166 if the enclosure 178 is manually assembled to the assembly 160 or by an automatic apparatus (not shown) in an automatic assembly system in a manufacturing environment. However, once the needle is passed through the cap, the assembly can be inserted into the enclosure merely by pushing on the hub during insertion. Once fully inserted, the enclosure squeezes the extension fixed in place against the hub.

Equivalent restraining forces on the needle cap assembly 160 and enclosure 178 in the axial or other directions may also be provided by apparatus in an automatic assembly system. For example, the enclosure may be restrained axially by an automatic apparatus as the needle assembly 160 is assembled to the enclosure also in the axial direction. The extension member, however, is preferably employed to restrain the cap compressed toward the hub during manual assembly.

In FIG. 24, the needle assembly 160 is shown fully compressed as installed in the enclosure 178. In this position, the sheath 164'is compressed and the hub 166 is closely received within the mating portion of the enclosure 178 cavity 180. The cap 162 abuts the shoulder 184. The thin strip extension member 170 passes out of the cavity 180 between the enclosure 178 collar 186 and the hub 166. The spacing between the enclosure collar 186 and the hub 166 is such that the extension member 170 is squeezed therebetween somewhat and applies the force F (FIG. 21) on the member 170, holding the sheath 164' in the compressed state. At this time external forces previously used to hold the sheath compressed are released.

In FIG. 19, a rear enclosure 188 receives the threaded hub portion 166' and a portion of the needle 168 protruding from the portion 166'. This assembly is for use with a syringe (not shown). The syringe has a finger grip spaced several inches from the hub. The hub portion 166' is threaded onto the syringe to form a complete assembly. The needle cap assembly has not yet been compressed to the needle ready stage of FIG. 24 for illustration only. Normally ,m the needle assembly would be compressed first as in FIG. 24. The enclosure 188 also receives the extension member portion 190 which may be folded or rolled over upon itself The rolled or folded portion 190 of the extension member is placed within the rear enclosure 188 and the rear enclosure is then attached to the front enclosure by a press friction fit of the rear enclosure end portion over the mating collar 186 of the front enclosure 178 as shown in FIG. 20.

In use, a user first removes the rear enclosure 188. This exposes the extension member 170 which is removed from the rear enclosure. The assembly thus appears as in FIG. 24. The hub portion 166' is then attached to the syringe. At this time the length of the extension member 170 is sufficiently great to extend over the syringe finger grip. At this time the user grasps the extension member and holds it while holding the finger grip by squeezing the extension member against the finger grip.

In the alternative, in the case of a multi sample needle used for drawing blood comprising a hollow cylindrical body or barrel in which vials are inserted each for separately receiving the drawn blood, the cap and sheath of the present invention may also be used. The barrel is connected to the threaded hub portion 166'. The user then squeezes the extension member(s) against the barrel to hold the cap in the needle ready position.

In a further alternative, in use with an intra-catheter using a catheter sheath and hub (not shown), the extension member(s) is squeezed against the intra-catheter body, which body forms the hub of the needle cap assembly as shown in FIG. 23 discussed in more detail below. The needle, sheath and cap are attached to the catheter body as an integral one piece molded plastic unit.

The grasping of the extension member holds the needle assembly in the compressed state as the front enclosure is then removed in reverse order ass discussed above. The compressed assembly is held in this state after the front enclosure is removed by the user maintaining relative forces on the extension member and the associated elements of the device in use. The needle is then used on a patient as described above. When the medical procedure is completed the operator releases the extension member and the cap 162 automatically extends over the needle tip and protects it.

FIGS. 16a and 16c show respectively a relatively stiff rod 190, FIG. 16d or a relatively stiff elongated flat member 192 of thermoplastic or other material which may be used as an extension member in the alternative to the film member 170 of FIG. 16. In these embodiments, the rod 190 or member 192 extend from the front enclosure through mating slots not shown) in the peripheral wall thereof at the collar 186 or in the hub 166, FIG. 166, FIG. 24. These extension members extend over the hub 166 and are enclosed by the rear enclosure having a mating configuration.

FIG. 22 shows a needle assembly 194 having a cap 196, a sheath 198, a hub 200 and a needle 206. Two elongated extension members 204 and 206 in the form of rods are attached (adhesive, one piece molded etc.) to the cap 196 at the rear edges of the sidewall 208. The members 204 and 206 are next adjacent to the hub 200 and may extend somewhat beyond the hub in the rearward axial direction. The entire assembly is then mounted in an enclosure which compresses the rod members 204 and 206 against the hub 200.

FIG. 23 shows the embodiment for use with an intra-catheter 211 wherein compressed needle assembly 210 has a hub 212 and a cap 214. A front enclosure 222 receives the needle assembly 210 with the needle 218 in the ready state. Two extension members 220 in the form of rods or other elongated stiff material extend from and are molded thermoplastic integral one piece with cap 214. The members 220 extend over the catheter body 213 in the assembled state with the front enclosure 222. The cap is held in the compressed state by the tapered cavity of the enclosure 222. The assembly is held in the compressed stated by engagement of the members 220 with the enclosure 222 and against the hub 2i2. Slots or grooves in the interior of the enclosure receive the members 220 for pressing the members 220 against the hub 166. When the enclosure 222 is removed, the user holds the members 220 against the body 213 to maintain the needle 2218 in the exposed ready to use state.

In FIG. 16a, cap 226 has an extension member 228 molded one piece therewith wherein the extension is a thin, i.e., about 0.010–0.100 inch thick elongated arcuate membrane. The member 228 is coplanar with the cap sidewall 229. In FIG. 16b, a pair of extension members 230 of similar dimensions as extension 228 are molded integral with the cap 232 on the outer peripheral surface 234 of cap 236 on opposite sides thereof.

In FIG. 25, a further embodiment comprises a needle assembly 240 being assembled to a front enclosure 242. Except for extension member 244, the needle assembly 240 may be the same as the needle assemblies as described above in connection with the embodiment of FIG. 16. The extension member 244 comprises an articulated rod including rod sections 246, 247 and 248 interconnected by respective articulating joints 250 and 252. The joints may comprise hinges formed by thinned portions between the rod sections which joints are manifested schematically in the figure as an enlarged region. Such thinned portions may be molded into the rod member 244 as living hinges as known in the plastic molding art. The extension member may then be folded in a retracted state when enclosed by the outer enclosures such as front enclosure 242 and a rear enclosure (not shown). One or more such rod extension members 244 may be provided according to a given implementation.

In some of the embodiments, the compliant outer corrugated resilient sheath may be shown spaced from the inner coil spring. This is a schematic representation as in practice the outer sheath 174 may be molded directly over the coil spring and assumes its corrugated shape by shrink fit on the coil spring turns so that the coil is in tight abutment with the outer sheath.

While a coil spring is shown for use with an outer resilient tubular sheath member, it will occur to one of ordinary skill that either the tubular outer member or inner coil spring may be used independently of the other element according to a given configuration. Typically the sheath is transversely weak so that the force of gravity on the cap displaces the cap offset from the needle longitudinal axis. The cap can generally be aligned with the needle manually or by separate apparatus (not shown).

Thus, it can be seen that a new and economical safety device is provided to health professionals in the utilization of virtually any type of syringe. The safety needle cap-sheath assembly of the invention can be supplied either for field connection to existing syringe and needle assemblies, or, of course, as a complete package including the needle and syringe. In use, the instant invention provides the new and important advantage of safely enclosing a potentially dangerous, used needle, automatically, without any necessity for conscious safety precautions on the part of the health professional.

While the present invention has been disclosed in connection with embodiments, various modifications and improvements will become readily apparent to those skilled in the art. Such disclosed embodiments are given by way of illustration and not limitation. Accordingly, the spirit and scope of the present invention is as set forth by the appended claims.

What is claimed is:

1. A safety needle cap assembly comprising:
   a hub;
   a needle attached to the hub;
   a safety needle cap having a first needle ready position and a second needle safety position, said cap having a pocket and including a front face portion having an opening through which the needle passes in the first position and side wall means connected to said front face portion and extending in a rearward direction from said front face portion;

a compressible resilient member having a first end connected to said safety needle cap and a second end secured to the hub portion for urging the cap to the second safety position;

at least one cap extension member secured to and extending substantially in the rearward direction from said safety needle cap towards and overlying the hub portion;

said safety needle cap being constructed to prevent the passage therethrough of the needle other than through said first opening, and when said cap is in the first pre-ready position with said resilient member compressed, and when said resilient member is then released, said cap is urged forward by the resilient member over the tip of the needle to the second safety position such that the tip of the needle is captured within the pocket of the cap; and an enclosure releasably secured to and about the hub and about at least a portion of said at least one extension member while said needle, said safety needle cap and said resilient member are in said first needle ready position, said at least one extension member extending between the hub and enclosure, the hub, extension member and enclosure being arranged so that the extension member is held to the hub by friction squeezing action of the enclosure to the hub for retaining the needle cap in the first needle ready position.

2. The safety cap needle assembly of claim 1 wherein the extension member extends rearwardly from said sidewall means.

3. The safety cap needle assembly of claim 2 wherein the extension member is coplanar with the sidewall means.

4. The safety cap needle assembly of claim 1 wherein the extension member is a pliable film.

5. The safety cap needle assembly of claim 1 wherein the extension member and cap are one piece integral thermoplastic material.

6. The safety cap needle assembly of claim 1 including a plurality of said extension members.

7. The safety cap needle assembly of claim 1 including a pair of said extension members secured to said cap.

8. The safety cap needle assembly of claim 1 wherein the extension member is flexible.

9. The safety cap needle assembly of claim 1 wherein the extension member is an elongated rod.

10. The safety cap needle assembly of claim 1 wherein the extension member is secured radially outwardly of and to said sidewall means.

11. The safety cap needle assembly of claim 1 wherein the extension member is an elongated pliable flap having a transverse width greater than its thickness.

12. The safety needle cap assembly of claim 1 wherein said safety needle cap further comprises:

(a) a rear face portion disposed along said side wall means a minimum distance rearwardly from said front face portion and connected to said side wall;

said rear face portion including a second opening having a second axis, said second axis axially offset from said first axis;

said second opening adapted to cooperate with the needle so as to position said safety needle cap in the pre-ready and released conditions, in an orientation, such that said first opening is not axially aligned with the axis of the needle.

13. The safety needle cap assembly claimed in claim 1 wherein said first opening is frusto-conical-shaped, the opening on the inside surface of said front face portion being smaller than the opening on the outside surface of said front face portion.

14. The safety needle cap assembly claimed in claim 13, wherein the opening in the front face portion has an outside surface and is of sufficient diameter such that body fluids adhering to said needle after withdrawal from the patient do not bridge the distance between the needle and the outside surface of said front face portion beyond the perimeter of the opening disposed on the outside surface of said front face portion.

15. The safety needle cap assembly claimed in claim 13, wherein an absorbent material is disposed in said frusto-conical opening.

16. The safety needle cap assembly claimed in claim 1 further comprising a Styrofoam material disposed about said opening and within said pocket, said Styrofoam material adapted to retain the tip of said needle when said needle is positioned in said pocket in the released condition.

17. The safety needle cap assembly claimed in claim 1 wherein said resilient member comprises an elastomeric material.

18. The safety needle cap assembly claimed in claim 1, wherein said resilient member comprises a spring enclosed in a sleeve of compliant material.

19. The safety needle cap assembly claimed in claim 17 wherein said elastomeric material is formed in an arc in its quiescent state.

20. A safety needle assembly comprising:

a hub;

a hollow needle having a tip and defining a longitudinal axis, the needle being attached to the hub at a needle portion distal the tip; and a safety needle cap sub-assembly attached to the hub comprising:

a cap with a front wall and a depending sidewall defining a pocket, said front wall having an opening therethrough for receiving the needle therethrough; and a resilient compressible member attaching the cap to the hub along the needle axis, the cap having a first normal quiescent needle safety position wherein the cap opening is positioned beyond the tip relative to the hub and wherein the resilient member is such that the cap normally is positioned so that the opening is displaced offset from the needle longitudinal axis for capturing the needle tip in the pocket, the cap having a needle ready second retracted position compressing the resilient member so the resilient member urges the cap toward the first normal needle safety position such that the needle passes through the cap opening and is exposed for use such that release of the cap from the retracted position permits the cap to displace to the first position; and an extension member extending rearwardly from the cap at the cap for restraining the cap in the needle ready second position; and an enclosure for the sub-assembly including an outer wall defining a cavity for receiving the cap, sheath, hub and a first portion of the extension member, a second portion of the extension member extending beyond the enclosure;

the extension member being juxtaposed with the hub and pressed to the hub by the enclosure to restrain the cap in the second position.

21. The assembly of claim 20 wherein the extension member is flexible.

22. The assembly of claim 20 wherein the extension member comprises a thermoplastic film.

23. The assembly of claim 20 wherein the extension is an elongated rod with at least one articulated joint.

24. The assembly of claim 20 wherein the extension member is a relatively stiff elongated element.

25. The assembly of claim 20 including at least one further extension member secured to the cap.

26. The assembly of claim 20 wherein the extension member is molded one piece integral with the cap.

* * * * *